United States Patent
Anderson

(10) Patent No.: US 7,410,011 B2
(45) Date of Patent: Aug. 12, 2008

(54) METHOD TO DETERMINE THE CONCENTRATION OF DEUTERIUM OXIDE IN A SUBTERRANEAN FORMATION

(75) Inventor: King Anderson, The Woodlands, TX (US)

(73) Assignee: Core Laboratories LP, Houston, TX (US)

( * ) Notice: Subject to any disclaimer, the term of this patent is extended or adjusted under 35 U.S.C. 154(b) by 0 days.

(21) Appl. No.: 11/375,680

(22) Filed: Mar. 14, 2006

(65) Prior Publication Data

US 2007/0215385 A1 Sep. 20, 2007

(51) Int. Cl.
*E21B 47/00* (2006.01)
*E21B 49/00* (2006.01)
*C09K 8/03* (2006.01)

(52) U.S. Cl. .................. 175/50; 166/250.12; 166/264; 175/42; 175/58; 175/59

(58) Field of Classification Search ................ None
See application file for complete search history.

(56) References Cited

U.S. PATENT DOCUMENTS

| | | | |
|---|---|---|---|
| 2,207,348 A | 7/1940 | Jones et al. ................ 436/29 |
| 2,869,642 A | 1/1959 | McKay et al. ......... 166/250.01 |
| 3,059,909 A | 10/1962 | Wise ......................... 261/39 |
| 3,180,142 A | 4/1965 | Bombardieri ............ 73/152.18 |
| 3,301,723 A | 1/1967 | Chrisp ........................ 149/20 |
| 3,316,965 A | 5/1967 | Watanabe ................... 166/280 |
| 3,492,147 A | 1/1970 | Young et al. ................... 427/5 |
| 3,632,316 A | 1/1972 | Kluge .......................... 23/307 |
| 3,711,598 A | 1/1973 | Babcock et al. ............. 423/580 |
| 3,789,112 A | 1/1974 | Pachaly ....................... 423/580 |
| 3,856,468 A | 12/1974 | Keller .......................... 436/27 |
| 3,888,312 A | 6/1975 | Tiner et al. .................. 166/308 |
| 3,981,977 A | 9/1976 | Mandel ...................... 423/580 |
| 4,035,475 A | 7/1977 | Richardson ................ 423/580 |
| 4,273,187 A | 6/1981 | Satter et al. ................. 166/250 |
| 4,352,674 A | 10/1982 | Fery ............................. 436/27 |
| 4,373,586 A | 2/1983 | Hunt, III .................... 166/263 |
| 4,411,798 A | 10/1983 | Chan .......................... 210/727 |
| 4,415,805 A | 11/1983 | Fertl et al. .................. 250/260 |
| 4,519,996 A | 5/1985 | Knochel et al. ............. 423/249 |
| 4,681,245 A | 7/1987 | Harvey ....................... 222/643 |
| 4,807,469 A | 2/1989 | Hall ........................ 73/152.19 |
| 4,840,292 A | 6/1989 | Harvey ........................... 222/1 |
| 5,049,743 A | 9/1991 | Taylor et al. ................ 250/303 |
| 5,077,471 A | 12/1991 | Smith, Jr. et al. ............ 250/260 |
| 5,246,860 A | 9/1993 | Hutchins et al. .............. 436/27 |
| 5,279,967 A | 1/1994 | Bode ........................... 436/56 |
| 5,410,152 A | 4/1995 | Gadeken .................... 250/260 |
| 5,830,763 A | 11/1998 | Junk et al. ..................... 436/56 |
| 5,929,437 A | 7/1999 | Elliott et al. ................ 250/259 |
| 5,986,030 A | 11/1999 | Murray et al. .............. 526/268 |
| 6,003,365 A | 12/1999 | Pope et al. ................ 73/152.39 |
| 6,016,191 A | 1/2000 | Ramos et al. ................. 356/70 |
| 6,025,200 A | 2/2000 | Kaish et al. .................. 436/56 |
| 6,075,611 A | 6/2000 | Dussan V. et al. ........... 356/432 |
| 6,076,046 A | 6/2000 | Vasudevan et al. ............ 702/12 |
| 6,110,373 A | 8/2000 | Patterson et al. |
| 6,125,934 A | 10/2000 | Lenn et al. ............. 166/250.12 |
| 6,148,913 A | 11/2000 | Collins ....................... 166/263 |
| 6,176,323 B1 * | 1/2001 | Weirich et al. ................ 175/40 |
| 6,192,985 B1 | 2/2001 | Hinkel et al. ................ 166/280 |
| 6,659,175 B2 | 12/2003 | Malone et al. ........... 166/250.1 |
| 6,912,898 B2 * | 7/2005 | Jones et al. .............. 73/152.11 |

OTHER PUBLICATIONS

Michael C. Adams et al.; *Thermal Stabilities of Aromatic Acids as Geothermal Tracers*, http://www.egi.utah.edu/geothermal/Tracer/T_Studies/, Sep. 21, 1998, pp. 1-23, 3 pages of references.

Michael C. Adams et al,; *The Dixie Valley, Nevada Tracer Test*, ESL—93011—PR, http://www.egi.utah.edu/geothermal/Tracer/T_Studies/, Mar. 3, 1998, Table of Contents, pp. 1-11, Appendix A, Appendix B.

Michael C. Adams et al.; *Kinetics of Fluorscein Decay and Its Application as a Geothermal Tracer*, http://www.egi.utah.edu/geothermal/Tracer/T_Studies/, Mar. 3, 1998, pp. 1-27.

(Continued)

*Primary Examiner*—Zakiya W. Bates
*Assistant Examiner*—Angela M DiTrani
(74) *Attorney, Agent, or Firm*—Madan, Mossman & Sriram, P.C.

(57) ABSTRACT

The extent of invasion of a water-based drilling fluid into a formation may be determined using at least two tracers where one is deuterium oxide and the other is a water-soluble tracer. One such method includes introducing a drilling fluid having an aqueous phase and known concentrations of a water-soluble tracer and deuterium oxide into a well drilled into a fluid-producing formation; obtaining a sample of the fluid from the fluid-producing formation at a location adjacent to the well; determining the concentrations of the deuterium oxide and water-soluble tracer in the sample; and calculating the deuterium oxide concentration within the fluid producing formation based on the known and determined concentrations of the water-soluble tracer and deuterium oxide in the drilling fluid and in the sample.

21 Claims, No Drawings

OTHER PUBLICATIONS

Michael C. Adams et al.; *The Application of Halogenated Alkanes as Vapor-Phase Tracers: A Field Test in the Southeast Geysers*, http://www.egi.utah.edu/geothermal/Tracer/T_Studies/, Mar. 3, 1998, 9 pgs.

Joseph J. Beall et al.; *R-13 Tracing of Injection in the Geysers*, http://www.egi.utah.edu/geothermal/Tracer/T_Studies/, Mar. 3, 1998, pp. 1-11.

Michael C. Adams et al., *Rhodamine WT as a Geothermal Tracer—A Field Test at Steamboat Hills, Nevada*, http://www.egi.utah.edu/geothermal/Tracer/T_Studies/, Mar. 3, 1998, 13 pgs.

Alcohols, http://www.egi.utah.edu/geothermal/Tracer/T_Studies/ ,Mar. 3, 1998.

Ofer Dahan et al.; *Analytical Procedure for Simultaneous Use of Seven Fluorobenzoates in Multitracer Tests*, vol. 39, No. 3, Ground Water, May-Jun. 2001, pp. 366-370, 2 Tables, 5 Figs.

T. Bjørnstad et al.; *Interwell Tracer Technology in Oil Reservoirs: State-of-the-Art*, pp. 261-268, 3 Tables, 2 Figs.

Tor Bjørnstad; *Recent and Current Oil Field Tracer Development for Interwell Application*, 2nd Tracer Workshop, University of Texas at Austin, Nov. 14 & 15, 1994, pp. 101-112, 2 Table, 18 Figs.

Joseph S. Tang; *Partitioning Tracers and In-Situ Fluid-Saturation Measurements*, SPE Formation Evaluation, Mar. 1995, pp. 33-39, 11 Figs.

Claus Ulrich Galdiga et al.; *Ultra trace determination of fluorinated aromatic carboxylic acids in aqueous reservoir fluids by solid phase extraction in combination with negative ion chemical ionisation mass spectrometry after derivatisation with pentafluorobenzyl bromide* Fresenius J. Anal Chem (1998) 361:797-802pp. 795-802, 3 Tables, 4 Figs.

Claus Ulrich Galdiga; *Trace Analysis of Fluorinated Aromatic Carboxylic Acids in Aqueous Reservoir Fluids by HPLC*, J. Liq. Chrom. & Rel. Technol., 21(6), pp. 855-868 (1998).

* cited by examiner

METHOD TO DETERMINE THE CONCENTRATION OF DEUTERIUM OXIDE IN A SUBTERRANEAN FORMATION

BACKGROUND

1. Field of the Invention

This invention relates to methods of distinguishing the source of water found in subterranean formations where oil and gas wells are drilled, and in particular to determining deuterium oxide concentrations in such formations.

2. Background Art

The use of so-called "tracers" in a variety of applications is well-known. "Tracers" represent a variety of chemical compounds that, under the conditions of use, act or react in a predictable way such that their presence, absence or activity in a particular location may be detected. This detection is useful in ascertaining and/or measuring events occurring at that location, i.e., in obtaining information about a particular microcosm such as, for example, a particular formation region at a drillsite.

Tracers that have traditionally been used in oil and gas drilling applications include, for example, salts of various types, such as potassium chloride. These materials operate to "tag", i.e., act as a tracer in, steam, oil, gas or water which is introduced into the subterranean formation or well-bore using any of a wide variety of known equipment and methods.

One application for tracers has been to track and quantify subterranean water migration, and in particular to track and quantify the infiltration of formations by drilling fluids. For example, it is known that, depending upon formation pressures, porosity and other variables, formations may be contaminated by significant amounts of drilling fluids. However, because this invasion may affect the accuracy of certain calculations and calibrations relating to oil and gas well preparation and production therefrom, it is desirable to be able to distinguish the effects of the infiltration from inherent formation characteristics.

This problem is particularly apparent when water-based drilling fluids are used in a formation that, itself, includes water. While known applications of certain tracers may confirm drilling fluid contamination of the formation, they generally cannot distinguish between the sources of the water in which they are carried. Because they may not distinguish the water source, calculations based on their presence in formation samples will not be entirely accurate. Because the calculations are essentially inaccurate, calibrations and other determinations based upon such calculations will have a margin of error. This margin of error may lead to non-optimal and even poor decisions relating to well management and production.

Thus, what is needed in the art is an improved method of ascertaining and measuring the infiltration of water-based drilling fluids into a subterranean formation, such that the source or sources of water in the formation may be distinguished.

SUMMARY

In one aspect there is provided a method of determining the concentration of deuterium oxide in a fluid-producing formation, comprising introducing a drilling fluid having an aqueous phase and known concentrations of a water-soluble tracer and deuterium oxide into a well drilled into a fluid-producing formation. A time sufficient for the drilling fluid to migrate into the fluid-producing formation, assuming such migration is possible, is allowed, and then a sample of fluid is obtained from the fluid-producing formation at a location adjacent to the well. From this sample the concentrations of the deuterium oxide and water-soluble tracer therein are determined. Finally, based on the known and determined concentrations of the water-soluble tracer and deuterium oxide in the drilling fluid and in the sample, the deuterium oxide concentration inherent to the fluid-producing formation is calculated.

DETAILED DESCRIPTION

In general, the method involves comparing the information obtained from knowing, detecting and/or otherwise determining concentrations of two distinct tracers introduced into an oil or gas well and, after a certain time period, in the subterranean formation adjacent thereto, in order to calculate therefrom the deuterium oxide "background concentration" in a formation fluid, i.e., the concentration naturally inherent therein. This allows the amount of deuterium oxide being contributed by a drilling fluid to be eliminated from calculations, which in turn allows the amount of water being contributed by a drilling fluid to be eliminated from the calculations. Thus, the accuracy of calculations and resultant calibrations for a wide variety of applications may be improved. This improvement may enable better management and production decisions and activities at the well-site.

The method generally employs at least two tracers. The first tracer is referred to hereinbelow as deuterium oxide, which is the entity that has been colloquially termed "heavy water". It is, in its relatively pure form, a compound formed of three atoms, in which one of the two hydrogen atoms contains one extra neutron, i.e., it is HDO rather than $H_2O$. Deuterium thus may be distinguished from hydrogen by virtue of its higher atomic mass. Deuterium oxide is naturally occurring, and is almost always present in natural waterways in varying amounts. These amounts frequently range from about 100 to about 200 ppm (parts per million), generally from about 120 to about 180 ppm, and most frequently from about 130 to about 160 ppm.

Various methods have been developed to prepare deuterium oxide, which is also a commercially available product. For example, distillation, condensation and electrolysis means may be employed in various ways for this purpose, resulting in concentration of deuterium oxide in ordinary water. Those skilled in the art of preparing deuterium oxide will be aware of various processes, such as that disclosed in, for example, U.S. Pat. No. 3,632,316 to Kluge, the entirety of which is incorporated herein by reference.

The second tracer is a water-soluble material. While deuterium oxide is also being used as a tracer, and is, indeed, water-soluble, hereinafter the term "water-soluble tracer" shall refer to only this second tracer, while the term "tracers" shall refer to both the deuterium oxide and the water-soluble tracer. This second tracer may be any water-soluble tracer, other than deuterium oxide, which is known to those skilled in the art to be suitable for "tagging" water molecules. For example, water-soluble tracers which may be selected include materials sold under the tradename SPECTRA-CHEM™, which are generally members of a family of compounds described as fluorobenzoic acid and salts thereof. These compounds are available from Protechnics, a division of Core Laboratories, and are known to be useful for downhole and formation tracer applications. Such useful tracers may also include, in non-limiting embodiments, salts such as potassium chloride. Thus, exemplary tracers may include, in non-limiting embodiments, 2-fluorobenzoic acid; 3-fluorobenzoic acid; 4-fluorobenzoic acid; 3,5-difluorobenzoic acid; 3,4-difluorobenzoic acid; 2,6-difluorobenzoic acid; 2,5-difluorobenzoic acid; 2,3-difluorobenzoic acid; 2,4-difluorobenzoic acid; pentafluorobenzoic acid; 2,3,4,5-tetrafluorobenzoic acid; 4-(trifluoromethyl)-benzoic acid; 2-(trifluoromethyl)benzoic acid; 3-(trifluoromethyl)benzoic acid; 3,4,5-trifluorobenzoic acid; 2,4,5-trifluorobenzoic acid; 2,3,4-trifluorobenzoic acid; 2,3,5-trifluorobenzoic acid; 2,3,6-trifluorobenzoic acid; 2,4,6-trifluorobenzoic acid; perfluoromethylcyclopentane (PMCP); perfluoromethylcyclohexane (PMCH); perfluorodimethylcyclobutane (PDMCB); m-per-fluorodimethylcyclohexane (m-PDMCH); o-perfluorodimethylcyclohexane (o-PDMCH); p-perfluorodimethylcyclohexane (p-PDMCH); perfluorotrimethylcyclo-hexane (PTMCH); perfluoro-ethylcyclohexane (PECH); perfluoroisopropylcyclohexane (IPPCH); combi-nations thereof; and the like.

Any water-soluble chemical compound, or mixture of compounds, may be used as a water-soluble tracer in the present invention, provided that (a) it is not already present at a measurable level in the reservoir/formation fluids of the well being tested; (b) it may be measured at levels sufficiently low as to allow its use to be economical; and (c) it does not interfere or interact undesirably with other materials present in the well at the levels used. In some non-limiting embodiments, the water-soluble tracer may be detectable at a range of from about 1 ppt (parts per trillion) to about 10,000 ppm in the formation fluid. In other non-limiting embodiments the water-soluble tracer may be detectable at a range of from about 5 ppt to about 1,000 ppm. In still other non-limiting embodiments the water-soluble tracer may be detectable at a range of from about 100 ppt to about 100 ppm. While concentrations greater than about 1000 ppm may be used, the selection of some water-soluble compounds at this usage level may be prohibitively expensive or result in unacceptable interactions with other materials present in the well environment.

The concentration of the deuterium oxide in the drilling fluid is desirably distinguishably greater than the expected "background", or inherent, concentration of deuterium oxide in the formation fluid. Deuterium oxide is present in most natural water sources in an amount of from about 100 to about 200 ppm, and more typically from about 120 ppm to about 180 ppm, and frequently from about 140 to about 160 ppm. Thus, it is likely that the drilling fluid itself, because it contains an aqueous phase, already has its own "background", or inherent, concentration of deuterium oxide. Because levels ranging up to about 200 ppm would be expected to also occur in subterranean water, and therefore also in formation fluids, it is desirable in many embodiments to increase the deuterium oxide level in the drilling fluid, via addition of deuterium oxide thereto, to a distinctive level. In some non-limiting embodiments this level is from about 200 to about 500 ppm, and in other non-limiting embodiments it is from about 250 to about 450 ppm. In still other non-limiting embodiments it is from about 250 to about 300 ppm. In many embodiments the deuterium oxide level in the drilling fluid may be from about 1.5 to about 3 times that of the naturally-occurring water. This means that, where the formation fluid is anticipated to be naturally in the range of from about 140 to about 160 ppm, the addition of deuterium oxide may be carried out to attain a deuterium oxide concentration in the drilling fluid of from about 210 to about 480 ppm. For reasons of economy and because of the relatively high cost of commercially available deuterium oxide, it may be desirable in many embodiments to employ a deuterium oxide concentration in the drilling fluid that is as low as possible, but still clearly distinct from the level expected to be naturally present in the formation fluid. This will require doping the drilling fluid with deuterium oxide.

Once the tracers have been selected and their desirable concentrations determined, they may be added to or incorporated in the appropriate drilling fluid by any means known to those skilled in the art to be operative or effective. It may be noted that drilling fluids that contain a particularly significant aqueous phase are often referred to as "water-based". However, even those drilling fluids referred to as "oil-based" drilling fluids may have some proportion of an aqueous phase therein, and therefore be operative in the present invention.

Because a comparison of the concentrations of water-soluble tracer and deuterium oxide in the drilling fluid and in the formation fluid is required herein, a sample of the formation fluid must be obtained. Obtention of this formation fluid sample may be done by any means typically, conventionally or otherwise used by or known to those skilled in the art. In some non-limiting embodiments, this may be done by sponge-coring at a location in the formation that is adjacent to the wellbore. This location is selected such that, if there is infiltration of the formation by the drilling fluid, and therefore contamination of the formation fluid, such will likely have occurred at the location of the sampling. Other means of obtaining a sample include, in additional non-limiting embodiments, any of various Repeat Formation Testing (RFT) methods, such as, for example, use of the MODULAR FORMATION DYNAMICS TESTER™ (MDT) (produced by Schlumberger) or the RESERVOIR CHARACTERIZATION INSTRUMENT$^{SM}$ (RCI) (produced by Baker Hughes). The sample may also be obtained by means of other types of coring, such as, in non-limiting embodiments, conventional, high torque, low invasion, high temperature/high pressure, horizontal, deepwater, gel, oriented, slimhole, and the like Once the sample has been obtained, analysis for the presence and concentrations of the selected tracers may be carried out. This analysis may be by any method known to be useful to those skilled in the art of doing such analyses. For example, in one method of analyzing for a fluorinated benzoic acid tracer, an emulsion of the formation fluid and naturally occurring inorganic materials is prepared, acidified with dilute hydrochloric acid, and then extracted using a nonpolar solvent. The organic phase is then admixed with a 1 N sodium hydroxide solution and then extracted with water. The water is then reacidified and extracted with methylene chloride. The recovered methylene chloride is then analyzed for the fluorinated benzoic acid tracer, optionally after being reduced in volume by evaporation. Alternatively, other organic solvents such as cyclohexane, n-hexane, pentane, benzene, or toluene may be used, provided that care is taken to ensure that the solvent does not have a significant background level of the water-soluble material selected as the tracer.

In the case of the fluorinated benzoic acid tracers, very low levels of tracer may alternatively be detected by taking advantage of the carboxylate group to first separate the tracer from non-acidic organics as a salt and then, in a second step, concentrating the tracer into an organic solvent by returning it to its acid form. It is then extracted from an aqueous phase.

There are also a number of instrumental methods that may be employed as part of the process to detect and measure the water-soluble tracer. These may include, but are not necessarily limited to, gas chromatography (GC) using flame ionization detectors, electron capture detectors, and the like; liquid chromatography (LC); infrared (IR) spectroscopy; mass spectroscopy (MS); combination instrumentation such as Fourier transform infrared (FTIR) spectroscopy, GC-MS, and LC-MS; and the like.

Analysis for the deuterium oxide may be conveniently and accurately accomplished via use of MS; GC-MS; oxygen, deuterium and hydrogen (ODH) analysis; and nuclear magnetic resonance (NMR) spectroscopy. However, the exhaustive extraction process that may be necessary to analyze for the water-soluble tracer may frequently be avoided in analyzing for the deuterium oxide. For example, where a sponge-core sample is obtained, separation of other formation fluid components from an analysis sample may be effectively carried out using, for example, a conventional Dean and Stark apparatus, an MDT instrument, or retort distillation. Because the Dean and Stark apparatus and method eliminates other water-soluble materials, including but not limited to the water-soluble tracer, from the analysis sample, only water and deuterium oxide is left. It is then possible to use the MS, GC-MS, ODH and/or NMR instrumentations and methods to directly analyze this sample for the deuterium oxide and/or deuterium.

When especially demanding analytical conditions arise, other means of doing the analyses may optionally be employed. These may include, but are not necessarily limited to, use of biologically active tracers for immunoassay, preparation of functional derivatives of the tracers by means such as esterification with more easily analyzed alcohols, and the like.

Finally, with all of the gathered and known concentration data, as described hereinabove, those skilled in the art will be able to determine what proportion, if any, of the water in the formation fluid is natural to the formation, and what proportion is derived from the drilling fluid, i.e., how much filtrate contamination of the formation is occurring. In general, it will be seen that detection of the water-soluble tracer in the sample indicates that the water-based drilling fluid has infiltrated the formation and the extent thereof. Determination of the concentration of deuterium oxide in the sample may then be used to determine what proportion of the water in the formation is water from the drilling fluid, and what proportion is water inherent to the formation.

In one embodiment a mathematical comparison may be accomplished using the equation:

EQUATION:

$$[D_2O_{sample}] = \frac{[T_{sample}][D_2O_{fluid}]}{[T_{fluid}]} + \frac{1-[T_{sample}][D_2O_{formation}]}{[T_{fluid}]}$$

In this equation the brackets indicate concentration, generally in ppm, and "T" indicates the water-soluble tracer. "Fluid" refers to the drilling fluid. Solving this equation for $[D_2O_{formation}]$ provides the "background concentration" of $D_2O$ in the formation fluid.

Once the deuterium oxide concentration of the formation has been determined, the information may be used in a variety of ways. In some non-limiting embodiments, the information may play a part in determining, for example, filtrate contamination level in core plugs that undergo Dean and Stark extraction, which enables correlation of the log to the formation, i.e., it provides the $R_w$ for the log calibration.

Those skilled in the art will appreciate that various modifications may be made to the description and embodiments hereinabove, within the scope of the invention as defined by the claims appended hereto. Many potential embodiments may be envisioned by those skilled in the art, including, for example, application to a wide variety of drillsite types, involving a wide variety of types of equipment and methods of analysis, and determinations involving a range of deuterium oxide and water-soluble tracer concentrations at various locations.

The following examples are provided to further illustrate the invention for the purpose of increasing the reader's overall understanding of it. As such they represent merely potential additional embodiments.

EXAMPLE 1

Hypothetical

Measured concentrations of deuterium oxide tracer (300 ppm deuterium) and of a fluorobenzoic acid water-soluble tracer (30,000 ppm) are added to a drilling fluid, e.g., a drilling mud, in the mud pit, and the drilling mud is then introduced into a subterranean formation via a well-bore. A sponge-core sample is then prepared using generally known sponge-coring techniques and equipment, and at an appropriate measured time after introduction of the tracers, such that at least a portion of the two tracers would be anticipated to have migrated to the vicinity of the core sample, assuming that formation characteristics are such that migration is possible. The sponge-core is then extracted to the surface, and the sponge liners appropriately preserved to ensure retention and protection of any fluids absorbed therein. A portion of the fluid is then removed, as a sample, from the sponge liner corresponding to one specific core location. This sample is analyzed by means that include use of GC-MS for the presence of the fluorobenzoic acid water-soluble tracer. The amount of tracer in the sample is found to be about 15,000 ppm. A portion of the water contained in the fluid is then removed from another sponge liner, corresponding to the same specific core location, by means of a Dean and Stark apparatus. This water is then analyzed for the presence of deuterium oxide using GC-MS. From this analysis it is determined that the deuterium oxide concentration of the fluid in the core is about 250 ppm. The following calculation is then carried out, based on the Equation hereinabove, as follows.

$$[250\ ppm] = \frac{[15,000\ ppm][300\ ppm]}{[30,000\ ppm]} + \frac{1-[15,000][D_2O_{formation}]}{[30,000\ ppm]}$$

Solving for $[D_2O_{formation}]$, it is found that the actual deuterium oxide concentration in the formation, i.e., the "background" deuterium oxide concentration, is 200 ppm.

What is claimed is:

1. A method of determining the concentration of deuterium oxide in a fluid-producing formation, comprising:
    introducing a drilling fluid having an aqueous phase and known concentrations of a water-soluble tracer and deuterium oxide into a well drilled into a fluid-producing formation;
    obtaining a sample of the fluid from the fluid-producing formation at a location adjacent to the well;
    determining the concentrations of the deuterium oxide and water-soluble tracer in the sample; and
    calculating the deuterium oxide concentration within the fluid-producing formation based on the known and determined concentrations of the water-soluble tracer and deuterium oxide in the drilling fluid and in the sample.

2. The method of claim 1 wherein the water-soluble tracer is selected from the group consisting of potassium chloride; 2-fluorobenzoic acid; 3-fluoro-benzoic acid; 4-fluorobenzoic acid; 3,5-difluorobenzoic acid; 3,4difluorobenzoic acid; 2,6-difluorobenzoic acid; 2,5-difluorobenzoic acid; 2,3-difluorobenzoic acid; 2,4-difluorobenzoic acid; pentafluorobenzoic acid; 2,3,4,5-tetrafluorobenzoic acid; 4-(trifluoromethyl)-benzoic acid; 2-(trifluoromethyl)-benzoic acid; 3-(trifluoromethyl)benzoic acid; 3,4,5-trifluorobenzoic acid; 2,4,5-trifluorobenzoic acid; 2,3,4-trifluorobenzoic acid; 2,3,5-trifluorobenzoic acid; 2,3,6-trifluorobenzoic acid; 2,4,6-trifluorobenzoic acid; perfluoromethyl-cyclopentane (PMCP): Perfluoro-methylcyclohexane (PMCH); perfluorodi-methylcyclo-butane (PDMCB); m-per-fluorodimethylcyclohexane (m-PDMCH); o-perfluorodimethylcyclohexane (o-PDMCH); p-perfluorodimethylcyclohexane (p-PDMCH); perfluorotrimethylcyclo-hexane (PTMCH); perfluoroethyl-cyclohexane (PECH); perfluoroisopropyl-cyclohexane (IP-PCH); and combinations thereof.

3. The method of claim 1 wherein the water-soluble tracer is used in an amount corresponding to from about 150 ppm to about 500 ppm, based on the drilling fluid.

4. The method of claim 1 wherein the deuterium oxide is in a concentration of from about 200 ppm to about 500 ppm, based on the drilling fluid.

5. The method of claim 1 wherein deuterium oxide is added to the drilling fluid prior to introducing the drilling fluid into the well.

6. The method of claim 1 wherein sampling is accomplished by a coring method selected from the group consisting of sponge, conventional, high torque, low invasion, high temperature/high pressure, horizontal, deepwater, gel, oriented, and slimhole.

7. The method of claim 1 wherein the concentration of deuterium oxide in the sample is determined using a method selected from the group consisting of Dean and Stark analysis and retort distillation.

8. The method of claim 7 wherein the concentrations of water-soluble tracer and deuterium oxide in the sample are determined using a method selected from the group consisting of gas chromatography (GC); liquid chromatography (LC); infrared (IR) spectroscopy; mass spectroscopy (MS); fourier transform infrared (FTIR) spectroscopy; or a combination thereof.

9. The method of claim 1 wherein the calculation of the deuterium oxide concentration in the formation is employed to calibrate a log.

10. A method of distinguishing a source of water present in fluid-producing formations, comprising:
doping a water-based drilling fluid with known amounts of deuterium oxide and a water-soluble tracer;
determining the concentrations of deuterium oxide and water-soluble tracer in the drilling fluid;
introducing the water-based drilling fluid into a well adjacent to a fluid-producing formation;
obtaining a sample from the fluid-producing formation;
determining the concentrations of deuterium oxide and water-soluble tracer in the sample; and
calculating the concentration of deuterium oxide within the fluid-producing formation based on the concentrations of deuterium oxide and water-soluble tracers in the drilling fluid and in the sample.

11. The method of claim 10 wherein the water-soluble tracer is selected from the group consisting of potassium chloride; 2-fluorobenzoic acid; 3-fluoro-benzoic acid; 4-fluorobenzoic acid; 3,5-difluorobenzoic acid; 3,4-difluorobenzoic acid; 2,6-difluorobenzoic acid; 2,5-difluorobenzoic acid; 2,3-difluorobenzoic acid; 2,4-difluorobenzoic acid; pentafluorobenzoic acid; 2,3,4,5-tetrafluorobenzoic acid; 4-(trifluoromethyl)-benzoic acid; 2-(trifluoromethyl)-benzoic acid; 3-(trifluoromethyl)-benzoic acid; 3-(trifluoro-methyl)benzoic acid; 3,4,5-trifluorobenzoic acid; 2,4,5-trifluorobenzoic acid; 2,3,4-trifluorobenzoic acid; 2,3,5-trifluorobenzoic acid; 2,3,6-trifluorobenzoic acid; 2,4,6-trifluorobenzoic acid; perfluoromethyl-cyclopentane (PMCP); perfluoro-methylcyclohexane (PMCH); perfluorodi-methylcyclo-butane (PDMCB); m-per-fluorodimethylcyclohexane (m-PDMCH); o-perfluorodimethylcyclohexane (o-PDMCH); p-perfluorodimethylcyclohexane (p-PDMCH); perfluorotrimethylcyclo-hexane (PTMCH); perfluoroethyl-cyclohexane (PECH); perfluoroisopropyl-cyclohexane (IP-PCH); and combinations thereof.

12. The method of claim 10 wherein the water-soluble tracer is used in an amount corresponding to from about 150 ppm to about 500 ppm, based on the drilling fluid.

13. The method of claim 10 wherein the deuterium oxide is in a concentration of from about 200 ppm to about 500 ppm, based on the drilling fluid.

14. The method of claim 10 wherein deuterium oxide deuterium oxide is added to the drilling fluid prior to introducing the drilling fluid into the well.

15. The method of claim 10 wherein sampling is accomplished by a coring method selected from the group consisting of sponge, conventional, high torque, low invasion, high temperature/high pressure, horizontal, deepwater, gel, oriented, and slimhole.

16. The method of claim 10 wherein the concentration of deuterium oxide in the sample is determined by a method selected from the group consisting of Dean and Stark analysis and retort distillation.

17. The method of claim 16 wherein the concentrations of deuterium oxide and water-soluble tracer in the sample are determined using a method selected from the group consisting of gas chromatography (GC); liquid chromatography (LC); infrared (IR) spectroscopy; mass spectroscopy (MS); Fourier transform infrared (FTIR) spectroscopy; or a combination thereof.

18. The method of claim 10 wherein the calculation of the deuterium oxide concentration in the formation is employed to calibrate a log.

19. A method of distinguishing a source of water present in fluid-producing formations, comprising:
doping a water-based drilling fluid with known amounts of deuterium oxide and a water-soluble tracer;
determining the concentrations of deuterium oxide and water-soluble tracer in the drilling fluid, such that the concentration of deuterium oxide is from about 200 ppm to about 500 ppm, and the concentration of the water-soluble tracer is from about 1 ppt to about 10,000 ppm;
introducing the water-based drilling fluid into a well adjacent to a fluid-producing formation;
obtaining a sample from the fluid-producing formation by means of sponge-coring;
determining the concentrations of deuterium oxide and water-soluble tracer in the sample; and
calculating the concentration of deuterium oxide within the fluid-producing formation based on the concentrations of deuterium oxide and water-soluble tracers in the drilling fluid and in the sample.

20. The method of claim 19 wherein the water-soluble tracer is selected from the group consisting of potassium chloride; 2-fluorobenzoic acid; 3-fluoro-benzoic acid; 4-fluorobenzoic acid; 3,5-difluorobenzoic acid; 3,4-difluorobenzoic acid; 2,6-difluorobenzoic acid; 2,5-difluorobenzoic acid; 2,3-difluorobenzoic acid; 2,4difluorobenzoic acid; pentafluorobenzoic acid; 2,3,4,5-tetrafluorobenzoic acid; 4-(trifluoromethyl)-benzoic acid; 2-(trifluoromethyl)-benzoic acid; 3-(trifluoro-methyl)benzoic acid; 3,4,5-trifluorobenzoic acid; 2,4,5-trifluorobenzoic acid; 2,3,4-trifluorobenzoic acid; 2,3,5-trifluorobenzoic acid; 2,3,6-trifluorobenzoic acid; 2,4,6-trifluorobenzoic acid; perfluoromethyl-cyclopentane (PMCP); perfluoro-methylcyclohexane (PMCH); perfluorodi-methyloyclo-butane (PDMCB); m-per-fluorodimethylcyclohexane (m-PDMCH); o-perfluorodimethylcyclohexane (o-PDMCH); p-perfluorodimethylcyclohexane (p-PDMCH); perfluorotrimethylcyclo-hexane (PTMCH); perfluoroethyl-cyclohexane (PECH); perfluoroisopropyl-cyclohexane (IP-PCH); and combinations thereof.

21. The method of claim 20 wherein the concentration of deuterium oxide in the drilling fluid is from about 250 to about 450, and the concentration of water-soluble tracer in the drilling fluid is from about 100 ppt to about 100 ppm.

* * * * *